(12) United States Patent
Babaev (10) Patent No.: US 7,785,278 B2
(45) Date of Patent: *Aug. 31, 2010

(54) APPARATUS AND METHODS FOR DEBRIDEMENT WITH ULTRASOUND ENERGY

(75) Inventor: Eilaz Babaev, Minnetonka, MN (US)

(73) Assignee: Bacoustics, LLC, Minnetonka, MN (US)

(*) Notice: Subject to any disclaimer, the term of this patent is extended or adjusted under 35 U.S.C. 154(b) by 358 days.

This patent is subject to a terminal disclaimer.

(21) Appl. No.: 11/857,162

(22) Filed: Sep. 18, 2007

(65) Prior Publication Data

US 2008/0004649 A1    Jan. 3, 2008

Related U.S. Application Data

(63) Continuation-in-part of application No. 11/880,321, filed on Jul. 20, 2007, now abandoned, which is a continuation-in-part of application No. 11/741,726, filed on Apr. 28, 2007, now abandoned, which is a continuation-in-part of application No. 11/449,220, filed on Jun. 7, 2006, now Pat. No. 7,431,704.

(51) Int. Cl.
*A61H 1/00* (2006.01)
*B05B 1/08* (2006.01)

(52) U.S. Cl. ....................... 601/2; 239/102.2

(58) Field of Classification Search .......... 601/2–4; 606/169; 239/102.2
See application file for complete search history.

(56) References Cited

U.S. PATENT DOCUMENTS

| | | | |
|---|---|---|---|
| 3,275,059 A | 9/1966 | McCullough | |
| 3,392,916 A | 7/1968 | Engstrom et al. | |
| 3,561,444 A | 2/1971 | Boucher | |
| 3,860,173 A | 1/1975 | Sata | |
| 4,052,004 A | 10/1977 | Martin et al. | |
| 4,085,893 A | 4/1978 | Durley, III | |
| 4,153,201 A | 5/1979 | Berger et al. | |
| 4,251,031 A | 2/1981 | Martin et al. | |
| 4,271,705 A | 6/1981 | Crostack | |
| 4,294,407 A | 10/1981 | Reichl et al. | |
| 4,301,093 A | 11/1981 | Eck | |
| 4,301,968 A | 11/1981 | Berger et al. | |
| 4,309,989 A | 1/1982 | Fahim | |

(Continued)

OTHER PUBLICATIONS

Babaev et al., First Experience of Using New Ultrasound Instrument for Treating Biological Tissue, article, 1973, pp. 57-59, 1st Ed. No. 165, Moscow Bauman School, Moscow, Russia.

(Continued)

*Primary Examiner*—Eric F Winakur
*Assistant Examiner*—Michael T Rozanski (57) ABSTRACT

An ultrasound surgical apparatus and associated methods of use enabling relatively pain-free wound debridement is provided. The apparatus is constructed from a tip mechanically coupled to a shaft. The shaft is mechanical coupled to an ultrasound transducer driven by a generator. The ultrasound tip possesses at least one radial surface, a cavity, or some other form of a hollowed out area, within at least one of the radial surfaces, and a cutting member at the opening of the cavity. A method of debriding a wound and/or tissue with the apparatus can be practiced by delivering ultrasonic energy released from the various surfaces of the vibrating tip to the wound and/or tissue prior to and/or while portions of the tip are scrapped across the wound and/or tissue.

17 Claims, 6 Drawing Sheets

U.S. PATENT DOCUMENTS

| | | | |
|---|---|---|---|
| 4,319,155 A | 3/1982 | Nakai et al. |
| 4,334,531 A | 6/1982 | Reichl et al. |
| 4,352,459 A | 10/1982 | Berger et al. |
| 4,428,531 A | 1/1984 | Martin |
| 4,466,571 A | 8/1984 | Muhlbauer |
| 4,530,360 A | 7/1985 | Duarte |
| 4,541,564 A | 9/1985 | Berger et al. |
| 4,582,654 A | 4/1986 | Karnicky et al. |
| 4,619,400 A | 10/1986 | Van Der Burgt |
| 4,642,581 A | 2/1987 | Erickson |
| 4,655,393 A | 4/1987 | Berger |
| 4,659,014 A | 4/1987 | Soth et al. |
| 4,679,551 A | 7/1987 | Anthony |
| 4,726,523 A | 2/1988 | Kokubo et al. |
| 4,726,525 A | 2/1988 | Yonekawa et al. |
| 4,733,820 A | 3/1988 | Endo et al. |
| 4,756,478 A | 7/1988 | Endo et al. |
| 4,783,003 A | 11/1988 | Hirabayashi et al. |
| 4,790,479 A | 12/1988 | Matsumoto et al. |
| 4,793,339 A | 12/1988 | Matsumoto et al. |
| 4,832,683 A | 5/1989 | Idemoto et al. |
| 4,850,534 A | 7/1989 | Takahashi et al. |
| 4,877,989 A | 10/1989 | Drews et al. |
| 4,905,671 A | 3/1990 | Senge et al. |
| 4,930,700 A | 6/1990 | McKown |
| 4,941,618 A | 7/1990 | Hildebrand et al. |
| 4,961,885 A | 10/1990 | Avrahami et al. |
| 5,002,059 A | 3/1991 | Crowley et al. |
| 5,040,537 A | 8/1991 | Katakura |
| 5,063,922 A | 11/1991 | Hakkinen |
| 5,076,266 A | 12/1991 | Babaev |
| 5,104,042 A | 4/1992 | McKown |
| 5,115,805 A | 5/1992 | Bommannan et al. |
| 5,134,993 A | 8/1992 | van der Linden et al. |
| 5,163,433 A | 11/1992 | Kagawa et al. |
| 5,172,692 A | 12/1992 | Kulow et al. |
| 5,186,162 A | 2/1993 | Talish et al. |
| 5,197,946 A | 3/1993 | Tachibana |
| 5,211,160 A | 5/1993 | Talish et al. |
| 5,231,975 A | 8/1993 | Bommannan et al. |
| 5,254,082 A | 10/1993 | Takase |
| 5,269,291 A | 12/1993 | Carter |
| 5,315,998 A | 5/1994 | Tachibana et al. |
| 5,316,000 A | 5/1994 | Chapelon et al. |
| 5,318,014 A | 6/1994 | Carter |
| 5,323,769 A | 6/1994 | Bommannan et al. |
| 5,324,255 A | 6/1994 | Passafaro et al. |
| 5,345,940 A | 9/1994 | Seward et al. |
| 5,347,998 A | 9/1994 | Hodson et al. |
| 5,362,309 A | 11/1994 | Carter |
| 5,374,266 A | 12/1994 | Kataoka et al. |
| 5,380,411 A | 1/1995 | Schlief |
| 5,393,296 A | 2/1995 | Rattner |
| 5,431,663 A | 7/1995 | Carter |
| 5,437,606 A | 8/1995 | Tsukamoto |
| 5,474,071 A | 12/1995 | Chapelon et al. |
| 5,515,841 A | 5/1996 | Robertson et al. |
| 5,515,842 A | 5/1996 | Ramseyer et al. |
| 5,516,043 A | 5/1996 | Manna et al. |
| 5,520,166 A | 5/1996 | Ritson et al. |
| 5,520,612 A | 5/1996 | Winder et al. |
| 5,526,815 A | 6/1996 | Granz et al. |
| 5,527,350 A | 6/1996 | Grove et al. |
| 5,529,572 A | 6/1996 | Spector |
| 5,545,124 A | 8/1996 | Krause et al. |
| 5,551,416 A | 9/1996 | Stimpson et al. |
| 5,554,172 A | 9/1996 | Horner et al. |
| 5,556,372 A | 9/1996 | Talish et al. |
| 5,573,497 A | 11/1996 | Chapelon |
| 5,616,140 A | 4/1997 | Prescott |
| 5,626,554 A | 5/1997 | Ryaby et al. |
| 5,643,179 A | 7/1997 | Fujimoto |
| 5,656,016 A | 8/1997 | Ogden |
| 5,658,323 A | 8/1997 | Miller |
| 5,699,805 A | 12/1997 | Seward et al. |
| 5,707,402 A | 1/1998 | Heim |
| 5,707,403 A | 1/1998 | Grove et al. |
| 5,720,287 A | 2/1998 | Chapelon et al. |
| 5,730,705 A | 3/1998 | Talish et al. |
| 5,735,811 A | 4/1998 | Brisken |
| 5,743,863 A | 4/1998 | Chapelon |
| 5,752,924 A | 5/1998 | Kaufman et al. |
| 5,762,616 A | 6/1998 | Talish |
| 5,785,972 A | 7/1998 | Tyler |
| 5,835,678 A | 11/1998 | Li et al. |
| 5,843,139 A | 12/1998 | Goedeke et al. |
| 5,879,314 A | 3/1999 | Peterson et al. |
| 5,879,364 A | 3/1999 | Bromfield et al. |
| 5,882,302 A | 3/1999 | Driscoll, Jr. et al. |
| 5,894,841 A | 4/1999 | Voges |
| 5,895,362 A | 4/1999 | Elstrom et al. |
| 5,947,921 A | 9/1999 | Johnson et al. |
| 5,960,792 A | 10/1999 | Lloyd et al. |
| 5,989,245 A | 11/1999 | Prescott |
| 6,001,069 A | 12/1999 | Tachibana et al. |
| 6,007,499 A | 12/1999 | Martin et al. |
| 6,014,970 A | 1/2000 | Ivri et al. |
| 6,024,718 A | 2/2000 | Chen et al. |
| 6,026,808 A | 2/2000 | Armer et al. |
| 6,027,495 A | 2/2000 | Miller |
| 6,041,253 A | 3/2000 | Kost et al. |
| 6,061,597 A | 5/2000 | Rieman et al. |
| 6,076,519 A | 6/2000 | Johnson |
| 6,083,159 A | 7/2000 | Driscoll, Jr. et al. |
| 6,095,141 A | 8/2000 | Armer et al. |
| 6,098,620 A | 8/2000 | Lloyd et al. |
| 6,102,298 A | 8/2000 | Bush et al. |
| 6,104,952 A | 8/2000 | Tu et al. |
| 6,106,547 A | 8/2000 | Huei-Jung |
| 6,113,558 A | 9/2000 | Rosenschein et al. |
| 6,113,570 A | 9/2000 | Siegel et al. |
| RE36,939 E | 10/2000 | Tachibana et al. |
| 6,158,431 A | 12/2000 | Poole |
| 6,176,839 B1 | 1/2001 | DeLuis et al. |
| 6,186,963 B1 | 2/2001 | Schwarze et al. |
| 6,190,315 B1 | 2/2001 | Kost et al. |
| 6,190,336 B1 | 2/2001 | Duarte et al. |
| 6,206,842 B1 | 3/2001 | Tu et al. |
| 6,206,843 B1 | 3/2001 | Iger et al. |
| 6,231,528 B1 | 5/2001 | Kaufman et al. |
| 6,234,990 B1 | 5/2001 | Rowe et al. |
| 6,251,099 B1 | 6/2001 | Kollias et al. |
| 6,273,864 B1 | 8/2001 | Duarte et al. |
| 6,296,630 B1 | 10/2001 | Altman et al. |
| 6,314,318 B1 | 11/2001 | Petty |
| 6,321,109 B2 | 11/2001 | Ben-Haim et al. |
| 6,322,527 B1 | 11/2001 | Talish |
| 6,325,769 B1 | 12/2001 | Klopotek |
| 6,371,903 B1 | 4/2002 | Blanc et al. |
| 6,478,754 B1 | 11/2002 | Babaev |
| 6,533,803 B2 | 3/2003 | Babaev |
| 6,569,099 B1 | 5/2003 | Babaev |
| 6,601,581 B1 | 8/2003 | Babaev |
| 6,623,444 B2 | 9/2003 | Babaev |
| 6,663,554 B2 | 12/2003 | Babaev |
| 6,716,184 B2 | 4/2004 | Vaezy et al. |
| 6,723,064 B2 | 4/2004 | Babaev |
| 6,761,729 B2 | 7/2004 | Babaev |
| 6,799,729 B1 | 10/2004 | Voic |
| 6,916,296 B2 | 7/2005 | Soring et al. |

| | | |
|---|---|---|
| 7,025,735 B2 | 4/2006 | Soring et al. |
| 7,431,704 B2 * | 10/2008 | Babaev .................... 601/2 |
| 2006/0241470 A1 | 10/2006 | Novak et al. |
| 2006/0241533 A1 | 10/2006 | Geller |

OTHER PUBLICATIONS

Babaev, The Qoustic Wound Therapy System (displaying model wound), sales literature released to the public Apr. 19, 2007.

Isakov, U; Loshcilov, V; Kleimenov, V; Babaev, E., First Experience of Using New Ultrasound Instrument for Treating Biological Tissue. Ultrasound in Surgery, Proceedings of Moscow Bauman School. 1st Ed. No. 165. 1973. p. 57-59.

Hsieh, Yueh-Ling, Effects of Ultrasound and Diclofenac Phonophoresis on Inflammatory Pain Relief: Suppression of Inducible Nitric Oxide Synthase in Arthritic Rats. Physical Therapy, vol. 86(1): 39-49. Jan. 2006.

* cited by examiner

APPARATUS AND METHODS FOR DEBRIDEMENT WITH ULTRASOUND ENERGY

CROSS REFERENCE TO RELATED APPLICATIONS

This application is a continuation-in-part of U.S. patent application Ser. No. 11/741,726 filed Apr. 28, 2007, the teachings of which are hereby incorporated by reference, which is a continuation-in-part of U.S. patent application Ser. No. 11/449,220, filed Jun. 7, 2006, the teachings of which are hereby incorporated by reference.

This application is also a continuation-in-part of U.S. patent application Ser. No. 11/465,300 filed Aug. 17, 2006, the teachings of which are hereby incorporated by reference, which is a continuation-in-part of U.S. patent application Ser. No. 11/449,220, filed Jun. 7, 2006, the teachings of which are hereby incorporated by reference

BACKGROUND OF THE INVENTION

1. Field of the Invention

The present invention relates to an apparatus and method for debriding wounds and/or various tissues of the body such as, but not limited to, tumors, epithelial tissue, muscle, and/or cartilage with ultrasound energy.

2. Description of the Related Art

When confronted with wounded tissue, physicians and similar practitioners of medical arts have numerous devices and methods at their disposal. Treating the wound can be simply accomplished by placing a bandage on the wound as to prevent contaminants such as, but not limited, microorganisms and dirt from entering the wound. Exposing the wound to hyperbaric oxygen may also bring about a therapeutic effect. More persistent and/or chronic wounds can be treated with repeated administrations of negative pressure therapy.

Administering pharmaceuticals to the wound may also be utilized to treat wounded tissue. A therapeutic benefit may be obtained by preventing an infection from developing in the wounded tissue. Keeping the wound in an infection free state can be accomplished by administering various anti-microbial agents such as, but not limited to, antiseptics, antibiotics, antiviral agents, antifungal agents, or any combination thereof. Administering various growth factors to the wounded tissue may also elicit a therapeutic benefit by promoting the growth of new tissue.

In extreme situations, the practitioner may have to resort to surgery to treat the wounded tissue. Grafting transplanted and/or bioengineered tissue onto the wounded may be necessary with severe wounds.

More experimental treatments, such as exposing the wounded tissue to ultraviolet light, electricity, and/or ultrasound, are also available to the practitioner. For example, U.S. Pat. Nos. 6,478,754, 6,761,729, 6,533,803, 6,569,099, 6,663,554, and 6,960,173 teach methods and devices utilizing an ultrasound generated spray to treat wounded tissues. Methods and devices utilizing indirect contact with the wounded tissue via a liquid aerosol are disclosed in U.S. Pat. Nos. 7,025,735 and 6,916,296. As taught by U.S. Patent Applications 2004/0030254 and 2006/0241470, directly contacting the wounded tissue with an ultrasonically vibrating probe may also be utilized to elicit a therapeutic effect by debriding the wound.

SUMMARY OF THE INVENTION

Treating severe and/or chronic wounds can be especially difficult. Successful treatment often requires the repeated removal of necrotic and/or diseased tissue by surgical debridement. The painful nature of surgical debridement, however, results in poor patient compliance. In the case of an infected and/or inflamed wound, surgical debridement procedures may be even more painful. Instead of enduring the pain of the cure, the patient chooses to live with the wound. Allowing the wound to go untreated, the patient becomes at risk for developing an infection and/or other complications. As the complications increase in severity, the patient may experience a reduced quality of life. For instance, an untreated diabetic ulcer on a patient's foot may become so painful that patient has difficulty walking.

An ultrasound surgical apparatus and associated methods of use enabling relatively pain-free wound debridement is provided. The apparatus comprises a tip mechanically coupled to a shaft. The shaft is mechanically coupled to an ultrasound transducer driven by a generator. The ultrasound tip comprises at least one radial surface, a cavity or some other form of a hollowed out area within at least one of radial surfaces, and a cutting member at the opening of the cavity.

When driven or otherwise activated by the generator, the ultrasonic transducer induces ultrasonic vibrations within the tip, causing ultrasonic energy to be released from the various surfaces of the tip. Directly contacting a wound and/or tissue with the vibrating tip causes the ultrasonic energy emanating from the various surfaces of the tip to enter the wound and/or tissue. The ultrasonic energy entering the wound and/or tissue reduces sensitivity to pain. Releasing ultrasonic energy into a wound and/or tissue is suspected, but not known, to change the permeability of cellular membranes to ions and/or other molecules within the extracellular environment. Changing membrane permeability may disrupt ionic and/or other chemical gradients relied upon by the cells to respond to painful stimuli.

When the transducer is activated, ultrasonic energy is also released from the walls of the cavity. Configuring the walls of the cavity as to form a parabola in at least two dimensions may focus the ultrasonic energy emanating from the walls of the cavity towards the focus of the parabola. If the focus of the parabola lies outside the cavity, then the ultrasonic energy emitted from the cavity may be concentrated towards a point below the surface of the wound and/or tissue to be treated. Concentrating the ultrasonic energy emitted from the cavity at a point below the surface of the wound and/or tissue may elicited a greater change in the membrane permeability of deep cellular structures such as, but not limited to, axons and somas, further decreasing the sensation of pain in the wound and/or tissue to be treated.

As to facilitate the transmission of ultrasonic energy from the walls of the cavity to a wound and/or tissue to be treated, the cavity may be filled with a coupling medium. Any fluid capable of conducting ultrasonic vibrations may be used as a coupling medium such as, but not limited to, saline, water, alcohol, corn oil, vegetable oil, or any combination thereof. When the tip is ultrasonically vibrated, cavitations may form within the coupling. Additionally or in the alternative, the coupling medium within the cavity may be atomized into a spray. If a piezoelectric transducer is used to induce the substructure formed by the shaft and tip, or just the tip if the shaft is omitted, to vibrate approximately in resonance, then the voltage of the electrical signal driving the transducer will largely control the degree to which the coupling medium is cavitated and/or atomized. At low voltages, the coupling medium within the cavity will be cavitated to a small degree. As the voltage increases, the amount of cavitations within the coupling medium is increased. Further increasing the voltage will eventually induce atomization of the coupling medium.

Regardless of whether the coupling medium within the cavity is atomized and/or cavitated, the presence of a coupling medium within the cavity may couple the transmission of ultrasonic energy released from the walls of the cavity to the wound and/or tissue to be treated.

Ultrasonic energy released from tip into the wound and/or tissue reduces sensitivity to pain. Thus by releasing ultrasonic energy into the wound and/or tissue prior to and/or simultaneously with debridement, the tip reduces the discomfort experienced by the patient during debridement. Various degrees of debridement may be achieved by scrapping various portions of the surgical apparatus across the wound and/or tissue. For example, scrapping cutting members secured to the tip across the wound and/or tissue aggressively debrides diseased, necrotic, and/or other unwanted tissue. Cutting members may be located at the opening of the cavity and/or on the various surfaces of the tip. Ultrasonic energy released from the cutting members and/or the vibrations of the cutting members may fragment and/or emulsify the tissue being debrided, which may reduce the amount of force needed to be applied to cutting members to perform debridement. Furthermore, the ultrasonic energy released from and/or the vibrations of the cutting members permits aggressive debridement with a dull cutting edge. A moderate degree of debridement may be achieved by scrapping blunt edges within the tip across wound and/or tissue to be treated. Scrapping smooth surfaces of the tip across the wound and/or tissue to be treated may produce a mild debridement.

It should be noted and appreciated that other therapeutic benefits and/or mechanisms of actions, in addition to those listed, may be elicited by devices and methods in accordance with the present invention. The mechanisms of action presented herein are strictly theoretical and are not meant in any way to limit the scope this disclosure and/or the accompanying claims.

DETAILED DESCRIPTION OF THE INVENTION

Figure 1:
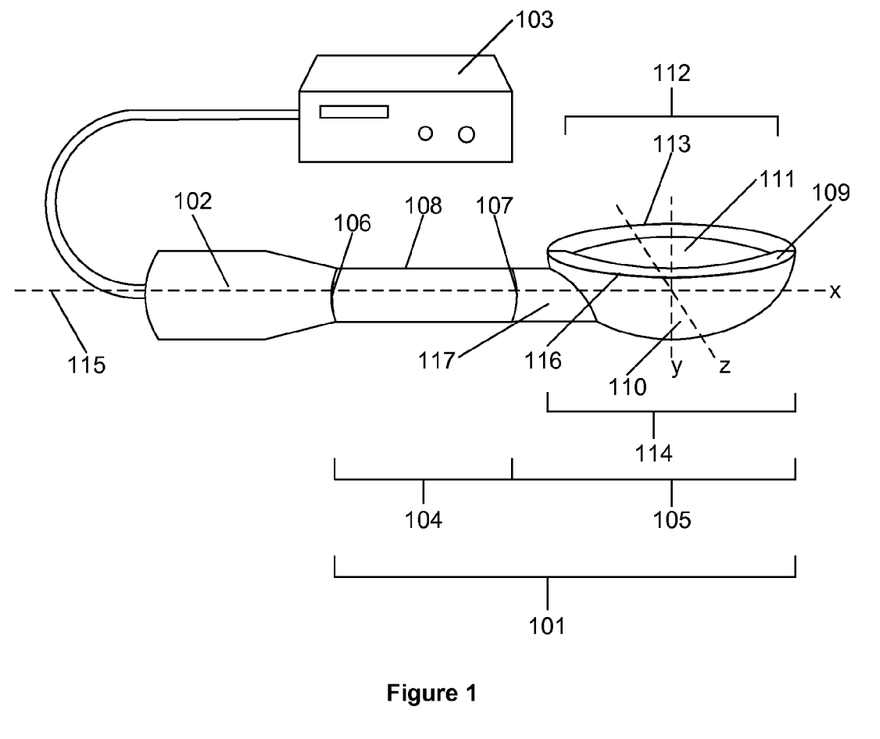
FIG. 1 is a perspective view of one embodiment of the surgical apparatus.

As illustrated by the embodiment depicted in FIG. 1, the surgical apparatus comprises a surgical substructure 101 attached to an ultrasound transducer 102 driven by an electrical signal produced by generator 103. As ultrasound transducers and generators are well known in the art, they need not, and will not for the sake of brevity, be described in detail herein. However, generator 103 should be capable of producing an electrical signal of a sufficient voltage to drive transducer 102 to induce substructure 101, or tip 105 if shaft 104 is omitted, to vibrate approximately in resonance, with the amplitude of the vibrations being between approximately 1 micron and approximately 100 microns. Surgical substructure 101 may be capable of vibrating approximately in resonance at a frequency between approximately 15 kHz and approximately 3 MHz. Preferably, substructure 101 should be capable of vibrating approximately in resonance at a frequency of approximately 30 kHz.

Surgical substructure 101 is comprised of shaft 104 and tip 105. As illustrated by the embodiment depicted in FIG. 1, shaft 104 contains a proximal surface 106 opposite a distal surface 107 and at least one radial surface 108 extending between proximal surface 106 and distal surface 107. The proximal surface 106 of shaft 104 is mechanically coupled to transducer 102. Distal surface 107 of shaft 104 is likewise mechanically coupled to tip 105. Mechanically coupled to transducer 102 and tip 105, shaft 104 transmits ultrasonic vibrations generated by transducer 102 to tip 105. Shaft 104 may be mechanically coupled to transducer 102 by mechanically attaching (for example securing with a threaded connection), adhesively attaching, and/or welding it to transducer 102. Alternatively, shaft 104 and transducer 102 may be a single piece. Likewise, shaft 104 may be mechanically coupled to tip 105 by mechanically attaching (for example securing with a threaded connection), adhesively attaching, and/or welding it to tip 105. Alternatively, shaft 104 and tip 105 may be a single piece. As to facilitate the mechanical attachment of shaft 104 to tip 105, tip 105 may, but need not, posses a shaft 117 or equivalent extension providing a point of attachment.

As illustrated by the embodiment depicted in FIG. 1, tip 105 comprises radial surfaces 109 and 110, a cavity 111 containing an opening 112 within the radial surface 109, and a cutting member 113 at opening 112. Though not illustrated, it would be possible for radial surface 110 to extend to opening 112 such that cavity 111 would open in radial surface 110. Providing a smooth edge that may be scrapped across a wound and/or tissue, radial surface 110 enables mild debridement. A moderate degree of debridement may be achieved by scrapping blunt edge 116 formed by the intersection of radial surfaces 109 and 110 across the wound and/or tissue to be treated. Scrapping cutting member 113 over a wound and/or tissue permits aggressive debridement. Though the particular cutting member 113 illustrated in FIG. 1 is formed by sharpening a region of radial surface 109 into an edge, the cutting member at the opening of the cavity need not be so fashioned. The cutting member may be a separate piece secured to a surface of tip 105 into which cavity 111 opens.

Figure 2:
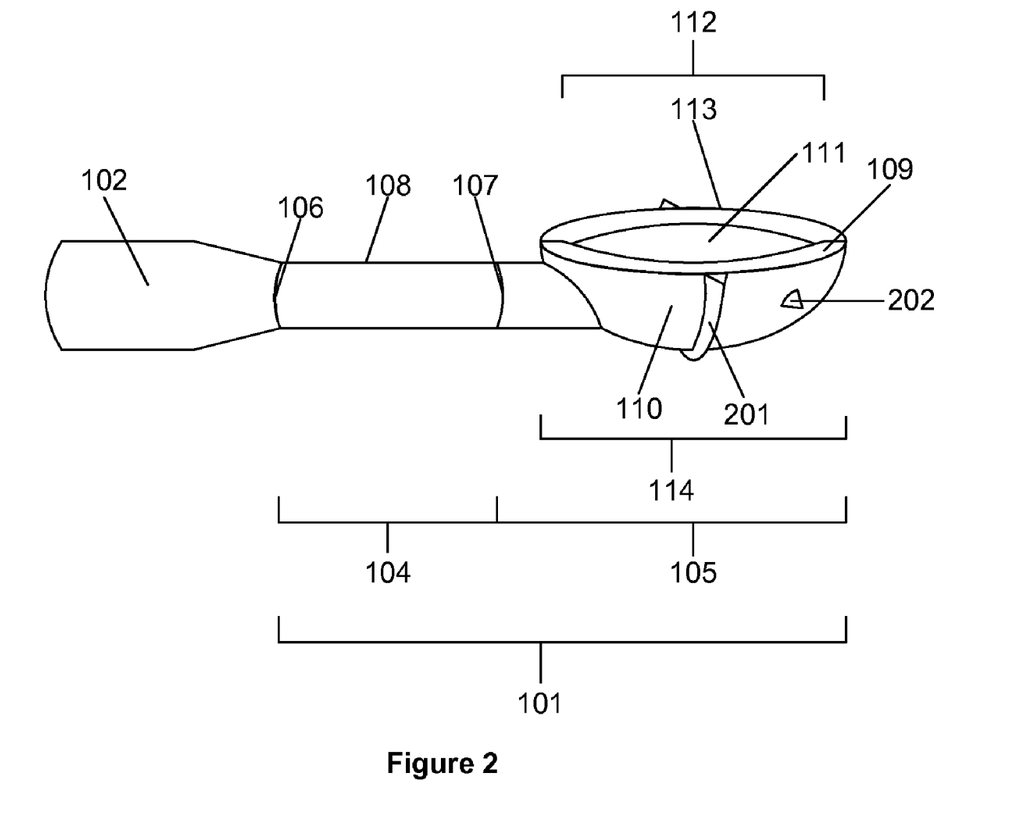
FIG. 2 depicts an embodiment of tip containing cutting edges affixed to a radial surface of the tip.

Aggressive debridement may also be achieved by scrapping a cutting member attached to at least one of the surfaces of the tip across the wound and/or tissue to be treated. FIG. 2 depicts an embodiment of tip 105 containing cutting edges 201 and 202 affixed to radial surface 110. As illustrated, cutting member 201 is sharpened into an edge, while cutting member 202 is sharpened into a point. Though sharpened to some degree, cutting members 113, 201, and 202 need not be so sharp as to cut and/or debride in the absence of ultrasonic vibrations. A plurality of cutting members may be attached to a surface of tip as to give the surface a rough and/or jagged appearance. Furthermore, cutting members attached to the surfaces of tip comprising a sharpened edge may run in any direction, and need not run the length of the surface to which they are attached.

Tip 105, as illustrated in FIGS. 1 and 2, may contain a region 114 that is wider than the shaft 104 in two dimensions (y and z) oriented orthogonal to the longitudinal axis 115 of shaft 104. Though not illustrated, it should be readily appreciated by those of ordinary skill in the art that tip 105 may be constructed as to possess a region wider than shaft 104 in only one dimension oriented orthogonal to longitudinal axis 115.

Furthermore, tip 105 may also be constructed as to lack any region wider than shaft 104 in a dimension oriented orthogonal to the longitudinal axis 115.

Figures 3A, 3B:
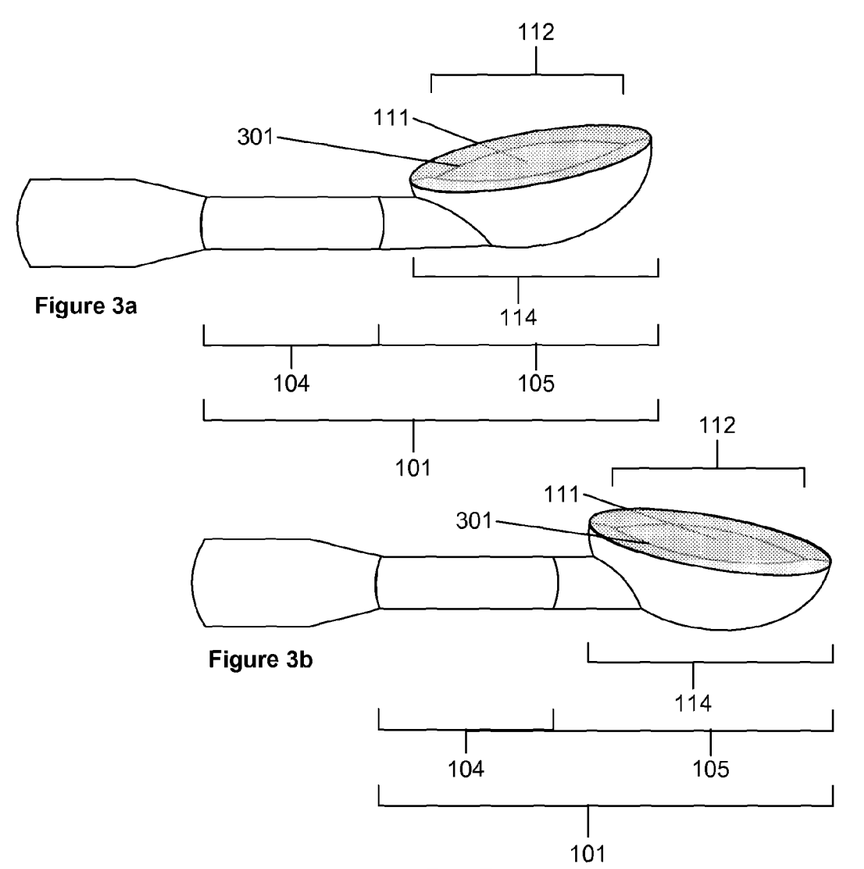
FIGS. 3a-3c illustrate embodiments of the apparatus depicting different possible configurations and orientations of the tip.

Radial surfaces 109 and 110 of the illustrated embodiment of tip 105 form a multidimensional parabola. As such, the illustrated embodiment of tip 105 is characterized by a general paraboloid structure. As illustrated by the embodiments depicted in FIGS. 3a and 3b, the plane 301 of opening 112 need not be parallel to the longitudinal axis 115 of shaft 104. It is also possible, as illustrated by the embodiment depicted in FIG. 3c, for the radial surfaces of the tip to form a two dimensional parabola. If the two dimensional parabola is extended in a third dimension, as illustrated in FIG. 3c, tip 105 may be characterized by a general vaulted configuration.

Figure 3C:
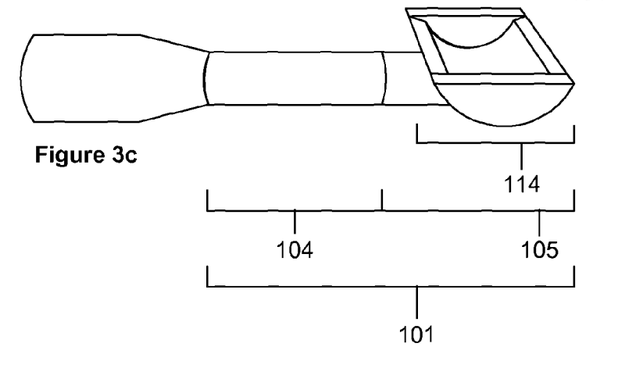
Figure 4:
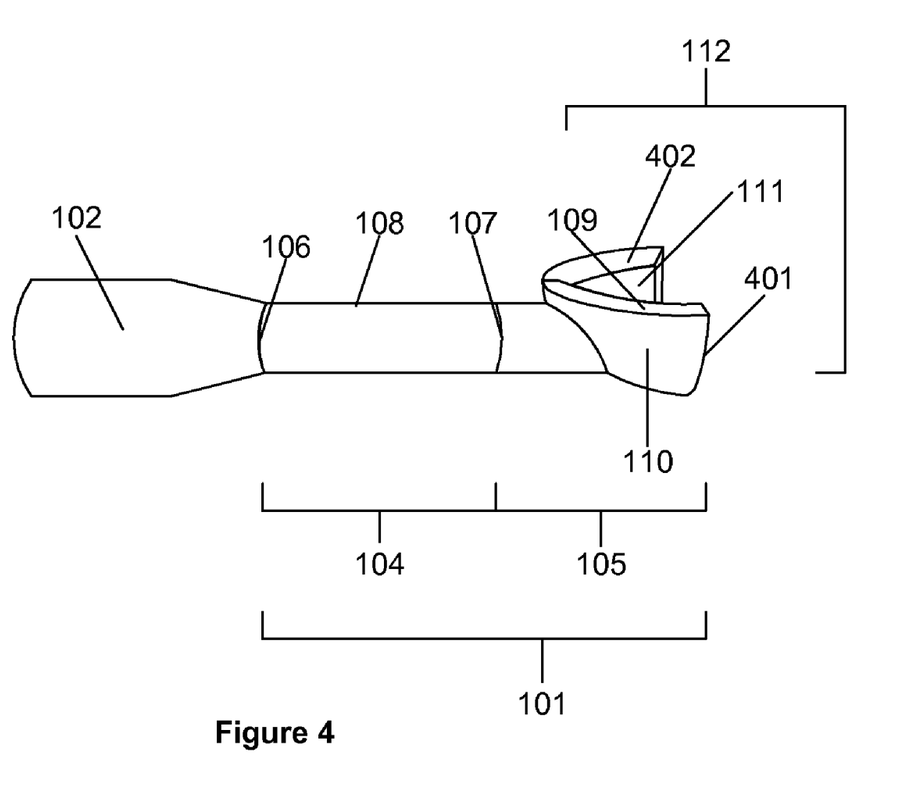
FIG. 4 illustrates an embodiment of the apparatus containing a distal surface.

It should be appreciated from FIG. 3c that the tip of the surgical apparatus may be comprised of more than two radial surfaces. Tip 105 may also contain a distal surface 401, as illustrated by the embodiment depicted in FIG. 4. In the depicted embodiment, opening 112 of cavity 111 extends from distal surface 401 to radial surface 109. The depicted cutting member 402 at the opening of cavity 111 is formed by sharpening a region of radial surface 109 and distal surface 401. As with the embodiment depicted in FIG. 1, cutting member 402 may be a separate piece secured to radial surface 109, distal surface 401, and/or any other surface into which cavity 111 opens. Furthermore, the cutting member however fashioned and/or formed need not extend onto an additional surface from that on which it originates.

Figure 5:
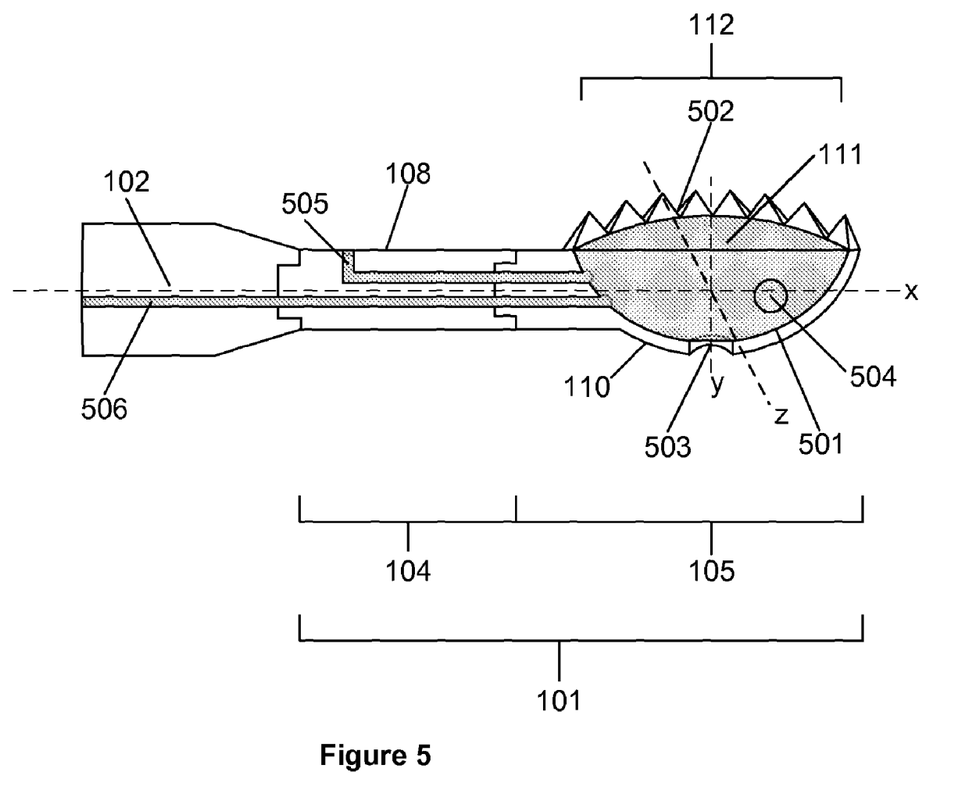
FIG. 5 illustrates a cross-sectional view of one embodiment of the surgical apparatus.

FIG. 5 illustrates a cross-sectional view of one embodiment of the surgical apparatus. As illustrated, wall 501 of cavity 111 may form a multidimensional parabola such that cavity 111 is characterized by a general paraboloid configuration. It is also possible, as illustrated in FIG. 3c, for the walls of cavity 111 to form a two dimensional parabola extended in a third dimension such that cavity 111 is characterized by a general vaulted configuration. In the embodiment illustrated in FIG. 5, the plurality of cutting members 502 encircling opening 112 of cavity 111 enables aggressive debridement. Moderate debridement may be achieved by scrapping the blunt edge provided the by the intersection of the inner surface of channel 503, located at the base of cavity 111, and radial surface 110 across the wound and/or tissue to be treated.

As to facilitate the transmission of ultrasonic energy emanating from the wall 501 of cavity 111 when a wound and/or tissue is debrided with a cutting member, edge, and/or surface at opening 112, cavity 111 may be filled with a coupling medium 504. Filling cavity 111 with coupling medium 504 may be made possible by delivering coupling medium 504 through channel 505, which contains an opening within radial surface 108 of shaft 104 and runs through a portion of the shaft 104 before opening within wall 501 of cavity 111, and/or channel 506, which extends through transducer 102 and shaft 104 before opening into cavity 111. In addition to filling cavity 111 with coupling medium 504, channel 505 and/or 506 may used to extract coupling 504 and/or debris accumulating in cavity 111 during debridement such as, but not limited to, fragmented and/or emulsified tissue.

Figure 6A:
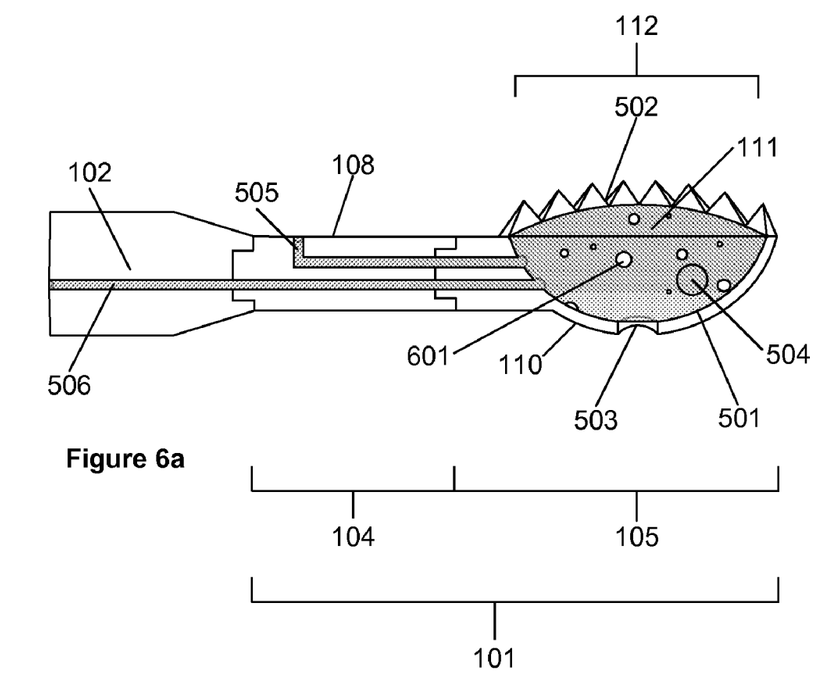
FIGS. 6a-6b illustrate an embodiments of the surgical apparatus in which the coupling medium within the cavity is cavitated and atomized.
Figure 6B:
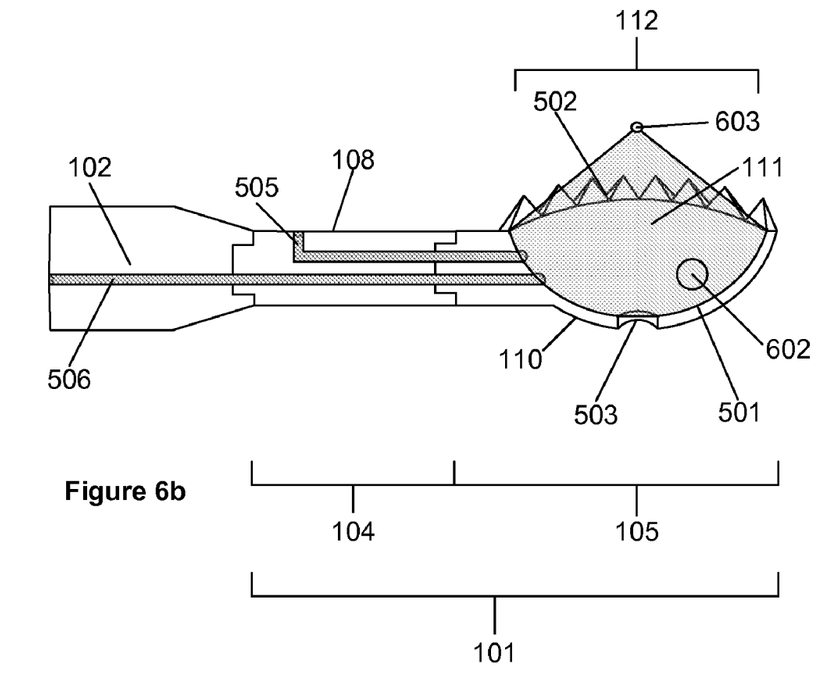

As depicted in FIG. 6a, cavitations 601 may be formed in coupling medium 504 if the generator driving transducer 102 produces an electrical signal of a sufficient voltage. If the voltage of the electrical signal is further increased, coupling 504 will atomize into spray 602. If the walls of cavity 111 form a parabola in at least two dimensions, atomized spray 602 and/or the ultrasonic energy emanating from the walls of cavity 111 may be focused towards focus 603 lying outside cavity 111. Positioning focus 603 outside cavity 111 may enable the ultrasonic energy emitted from the walls of cavity 111 to be concentrated towards a point below the surface of the wound and/or tissue being treated. Focus 603 may also be positioned within cavity 111 or in the plane of opening 112.

It should be appreciated that elements described with singular articles such as "a", "an", and/or "the" and/or otherwise described singularly may be used in plurality. It should also be appreciated that elements described in plurality may be used singularly.

Although specific embodiments of apparatuses and methods have been illustrated and described herein, it will be appreciated by those of ordinary skill in the art that any arrangement, combination, and/or sequence that is calculated to achieve the same purpose may be substituted for the specific embodiments shown. It is to be understood that the above description is intended to be illustrative and not restrictive. Combinations of the above embodiments and other embodiments as wells as combinations and sequences of the above methods and other methods of use will be apparent to individuals possessing skill in the art upon review of the present disclosure.

The scope of the claimed apparatus and methods should be determined with reference to the appended claims, along with the full scope of equivalents to which such claims are entitled.

I claim:

1. An apparatus comprising a:
    a. a shaft containing:
        i. a proximal surface opposite a distal surface,
        ii. at least one radial surface extending between the proximal surface and the distal surface, and
        iii. a longitudinal axis extending through the shaft from the proximal surface to the distal surface;
    b. a tip attached to the distal surface of the shaft containing:
        i. at least one radial surface;
        ii. a paraboloid cavity containing at least one wall and an opening within at least one of the radial surfaces of the tip wherein the plane of the opening is not orientated orthogonal to the longitudinal axis of the shaft; and
        iii. a sharpened cutting member or plurality of sharpened cutting members at the opening of the cavity;
    c. a channel or plurality of channels running through at least a portion of the shaft containing an opening within a surface of the shaft and opening within a wall of the cavity; and
    d. a coupling medium delivered to the cavity through at least one of the channels opening within a wall of the cavity.

2. The apparatus of claim 1 further comprising a region of the tip wider than the shaft in at least one dimension oriented orthogonal to the longitudinal axis of the shaft.

3. The apparatus according to claim 1 wherein said shaft and said tip are characterized by being capable of vibrating in combination approximately in resonance at a frequency between approximately 15 kHz and approximately 3 MHz.

4. The apparatus of claim 1 wherein said shaft and said tip are characterized by being capable of vibrating in combination approximately in resonance at a frequency of approximately 30 kHz.

5. The apparatus of claim 1 further comprising a parabola formed by the radial surfaces of the tip in at least two dimensions.

6. The apparatus of claim 1 characterized by the focus of the paraboloid cavity of the tip lying outside the cavity.

7. The apparatus of claim 1 further comprising at least one additional cutting member on at least one of the radial surfaces of the tip.

8. The apparatus of claim 1 further comprising at least one distal surface on the tip.

9. The apparatus of claim 8 further comprising a distal opening to the cavity of the tip within at least one of the distal surfaces on the tip.

10. The apparatus of claim 9 further comprising an additional cutting member on the distal surface on the tip at the distal opening of the cavity.

11. The apparatus of claim 1 further comprising an ultrasound transducer attached to the proximal surface of the shaft.

12. The apparatus of claim 11 further comprising an additional channel or plurality of channels extending through at least a portion of the transducer and communicating with the channel or plurality of channels extending through the shaft and opening into the cavity.

13. The apparatus of claim 11 further comprising a generator capable of producing an electrical signal of a sufficient voltage to drive the transducer to induce the substructure formed by the shaft and tip to vibrate.

14. The apparatus according to claim 13 characterized by the generator being capable of producing an electrical signal of a voltage sufficient to induce the substructure formed by the shaft and tip to vibrate approximately in resonance with the amplitude of the vibrations being between approximately 1 micron and approximately 100 microns.

15. The apparatus according to claim 13 characterized by the generator being capable of producing an electrical signal of a voltage sufficient to induce the substructure formed by the shaft and tip to vibrate approximately in resonance with the amplitude of the vibrations being approximately 100 microns.

16. The apparatus according to claim 13 characterized by the generator being capable of producing an electrical signal of a voltage sufficient to induce cavitations within the coupling medium.

17. The apparatus according to claim 13 characterized by the generator being capable of producing an electrical signal of a voltage sufficient to atomize the coupling medium.

* * * * *